United States Patent [19]

Foss

[11] Patent Number: 4,905,702

[45] Date of Patent: Mar. 6, 1990

[54] APPARATUS FOR IMAGING AND MEASURING PORTIONS OF SKIN

[76] Inventor: Pierre N. Foss, Rodener Strasse 16, D-6630 Saarlouis, Fed. Rep. of Germany

[21] Appl. No.: 165,596

[22] Filed: Mar. 8, 1988

[51] Int. Cl.⁴ .................................................. A61B 6/08
[52] U.S. Cl. ...................................... 128/665; 358/93; 358/229; 362/804
[58] Field of Search ............... 128/665, 630, 653, 743; 358/229, 93; 362/11, 804

[56] References Cited

U.S. PATENT DOCUMENTS

| | | | |
|---|---|---|---|
| 2,437,916 | 3/1948 | Greenwald | 128/665 |
| 3,891,842 | 6/1975 | Strusinski | 358/229 |
| 4,170,987 | 10/1979 | Anselmo et al. | 128/665 |
| 4,638,798 | 1/1987 | Shelden et al. | 128/653 |
| 4,693,255 | 9/1987 | Beall | 128/665 |

*Primary Examiner*—Francis Jaworski
*Assistant Examiner*—John C. Hanley
*Attorney, Agent, or Firm*—Peter K. Kontler

[57] ABSTRACT

Apparatus for contact-free imaging and measuring of a selected portion of the skin of a patient has a camera which is mounted on a support. The support is mounted on a holder so that it can move in the direction of as well as that it can turn about the optical axis of the camera. An annular light source on the support surrounds the objective of the camera, and the support is connected with an arcuate carrier of one, two or more additional light sources serving to illuminate that portion of the skin which is to be imaged by the camera. The latter can be connected to an electronic evaluating system including a computer, a video camera and/or a monitor which displays the images of the selected portion of the skin. The light source or sources on the carrier are adjustable relative to the carrier and relative to the selected portion of the skin, and the carrier is adjustable with reference to the support along an arcuate path. The carrier is provided with mechanisms and/or instruments for adjusting the intensity, direction, color and/or other characteristics of light which is emitted by the light source or sources on the carrier. The positions of the support, carrier and light sources are recorded for later use and/or for perusal by persons other than the person in charge of imaging the selected portion of the skin.

10 Claims, 8 Drawing Sheets

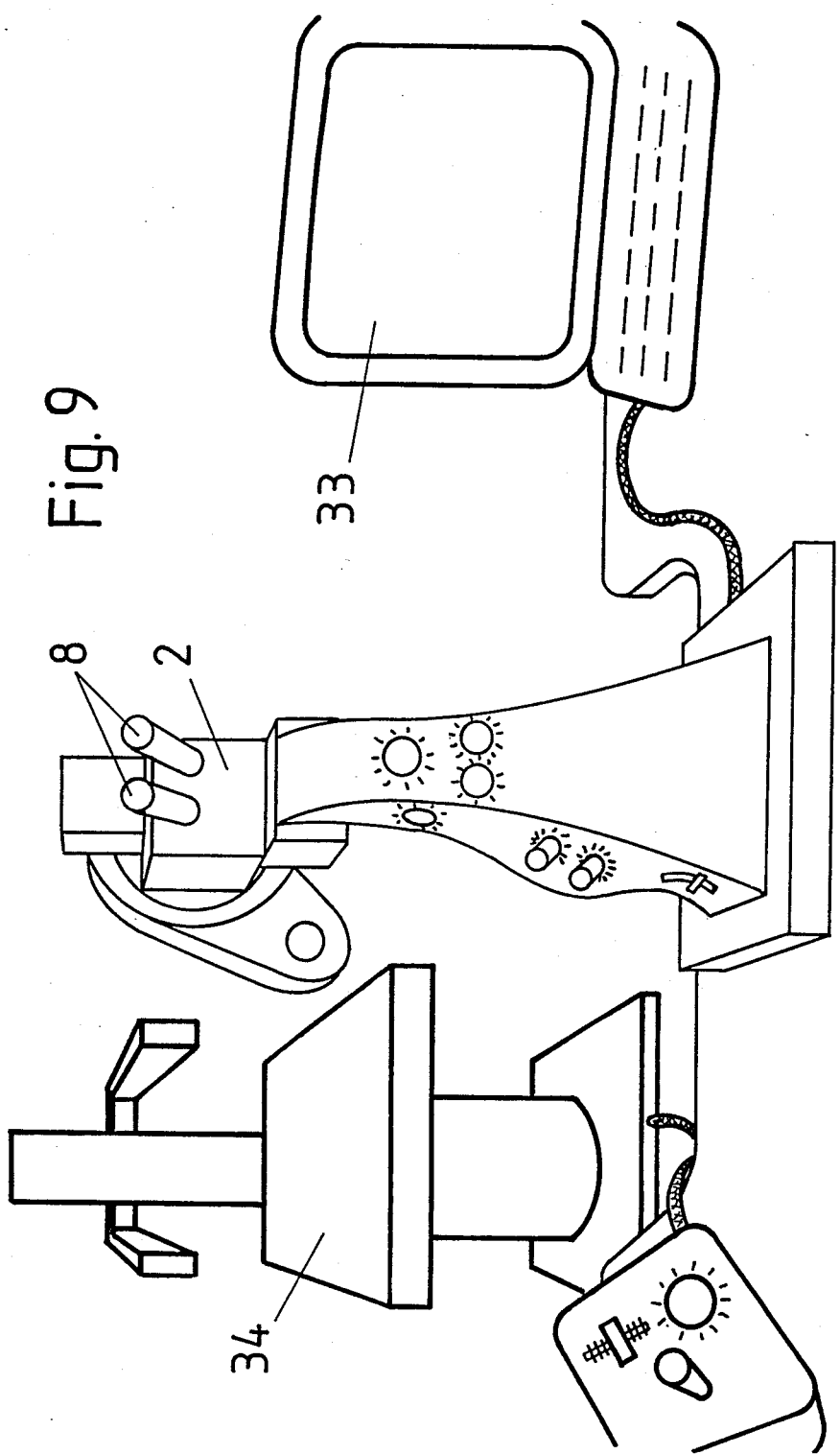

APPARATUS FOR IMAGING AND MEASURING PORTIONS OF SKIN

BACKGROUND OF THE INVENTION

The invention relates to apparatus for imaging selected portions of animal bodies, especially for imaging selected portions of the skins of human patients. More particularly, the invention relates to apparatus for contact-free imaging and measuring of selected portions of skin, for example, discolored, bruised, cut, frozen, swollen, diseased and/or otherwise affected portions of skin.

Afflicted portions of skin are usually subjected to visual examination by a physician who makes a written record of the results of examination to describe the condition of the inspected portion of the skin. Such examination is subjective and the terminology which is employed to describe the condition of an affected skin portion varies from physician to physician. For example, a physician is likely to describe an afflicted skin portion as having the size of a cherry pit, being of a reddish-violet color or in similar terms which might not be sufficiently meaningful to another physician. Moreover, such subjective description cannot be used to make valid comparisons as the condition of the affected skin portion varies from hour to hour, from day to day or from visit to visit. On the other hand, an accurate comparison of the condition of an afflicted skin portion during successive examinations is highly desirable and advantageous because it ensures timely detection of malignant skin portions and/or to readily distinguish malignant afflictions from benign ailments.

U.S. Pat. No. 4,535,782 to Zoltan discloses an apparatus which is used for non-contacting volume determination of wounds, particularly decubitus ulcers. The apparatus of Zoltan employs a cubical reference object which is placed next to the afflicted part of the skin and is imaged on a grid of lines to facilitate a determination of the dimensions of the afflicted area. The versatility of the patented apparatus is insufficient to allow for accurate and rapid imaging of any selected portion of the skin.

OBJECTS AND SUMMARY OF THE INVENTION

An object of the invention is to provide an apparatus which can be used with advantage for diagnostic purposes and serves for contact-free imaging and measurement of selected portions of skin in such a way that a comparison of records made at desired intervals enables the physician to accurately determine the progress of the disease and/or healing on the basis of an inspection of measurements and/or pictures taken at such desired intervals.

Another object of the invention is to provide a versatile apparatus which can be rapidly set up to allow for imaging and maasurement of hard-to-inspect portions of the skin.

A further object of the invention is to provide the apparatus with novel and improved means for illuminating the selected portion of the skin and with novel and improved means for recording the information which is gathered as a result of imaging and/or measurement of the selected skin portion.

An additional object of the invention is to provide the apparatus with novel and improved means for focusing the imaging unit upon the selected portion of the skin and with novel and improved means for recording the positions of all movable parts or of selected movable parts to thus facilitate renewed positioning of the imaging unit and light source or sources in the same way as during a preceding examination.

Still another object of the invention is to provide a novel and improved method of recording the condition of a selected portion of the skin for future reference, especially for comparison with recordings made on one or more previous occasions.

A further object of the invention is to provide the apparatus with novel and improved means for influencing one or more characteristics of light which is directed upon the selected portion of the skin.

An additional object of the invention is to provide an apparatus which can be used for imaging and/or for transillumination of selected portions of skin.

The invention resides in the provision of an apparatus for contact-free imaging and measurement of portions of skin, especially for diagnostic purposes. The improved apparatus comprises at least one imaging unit (such as a camera) having an optical axis and serving to be trained upon a selected portion of the skin (e.g., upon a diseased, bruised, discolored and/or otherwise afflicted portion of the skin), a support member for the imaging unit, and a carrier member mounted on the support member (or vice versa). At least one of these members is movable in the direction of and relative to the optical axis, and the apparatus further comprises means for at least temporarily recording the position of the at least one member, and illuminating means including at least one light source (such as a flash unit) provided on at least one of the members and serving to illuminate the selected portion of the skin.

The carrier member can include or constitute a suitably curved part which extends along an arc of at least 90°, preferably along an arc of more than 180°, and is movable relative to the support member. The center of curvature of the arc is preferably on or close to the optical axis, and the at least one light source can be mounted on the carrier member. The latter is preferably provided with a slide and/or with other suitable means for moving the at least one light source along the arc and/or toward and away from the center of curvature. The skin portion which is to be imaged and/or measured is preferably located at or very close to the center of curvature when the apparatus is ready for use.

It is preferred to provide the apparatus with several light sources, namely with at least one light source on the carrier member and with at least one light source on the support member. The latter light source is preferably designed to at least partially surround the imaging unit and to direct light upon the selected portion of the skin.

The apparatus can further comprise a holder (e.g., a floor-mounted stand) for the support member, and the support member and/or the imaging unit is preferably rotatable relative to the holder about the optical axis and/or movable relative to the holder in the direction of the optical axis. The imaging unit preferably shares at least some movements of the support member relative to the holder.

The apparatus can further comprise means for influencing at least one characteristic of light which is emitted by the at least one source, such as the intensity, color, direction and/or quantity of light. The influencing means can be mounted on the carrier member which latter can support one, two or more discrete light sources each of which is adjustable relative to the carrier member independently of the other light source or sources so as to ensure that each light source can be moved to an optimum position with reference to the selected portion of the skin.

The apparatus can further comprise a computer, a video camera and/or a monitoring device operatively connected with the imaging system. The computer can process the information which is furnished by the imaging unit, and the monitoring device can display the images of the selected portion of the skin.

The apparatus can further comprise means (e.g., rack and pinion drives, mating gears, links, levers and/or others) for moving the carrier member relative to the support member and/or vice versa, for moving the support member relative to the holder and/or for moving the imaging unit relative to the support member and/or for moving the at least one light source relative to the carrier member and/or support member and/or for rotating the support member and/or the carrier member about the optical axis.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 9 is a schematic perspective view of the apparatus with a minotor and seating facility but with the carrier member omitted for the sake of clarity.

DESCRIPTION OF THE PREFERRED EMBODIMENTS

Figure 1:
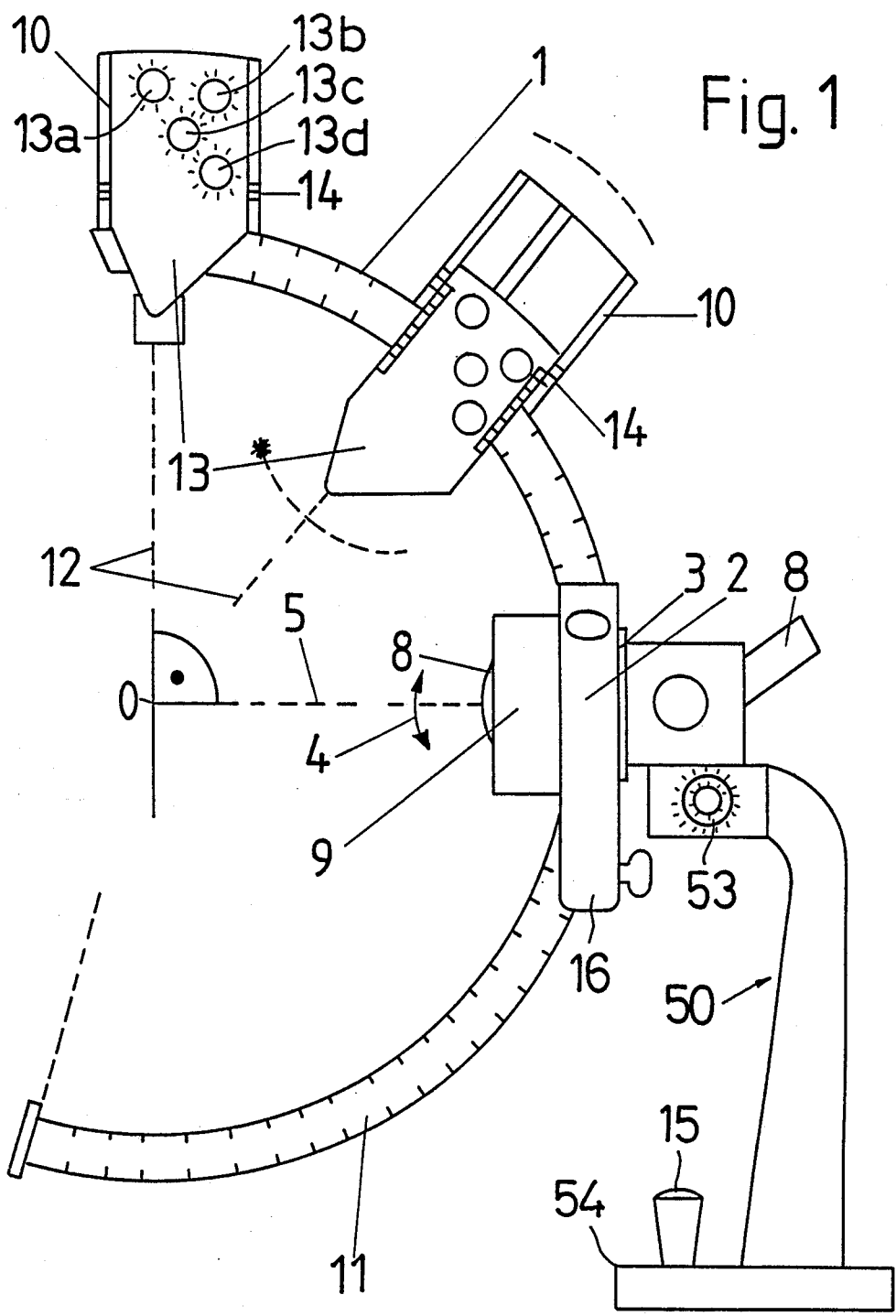
FIG. 1 is a schematic elevational view of an apparatus which embodies one form of the invention, the carrier member being shown in a substantially vertical plane and the imaging unit on the support member being trained upon a selected portion of the skin.
Figure 2:
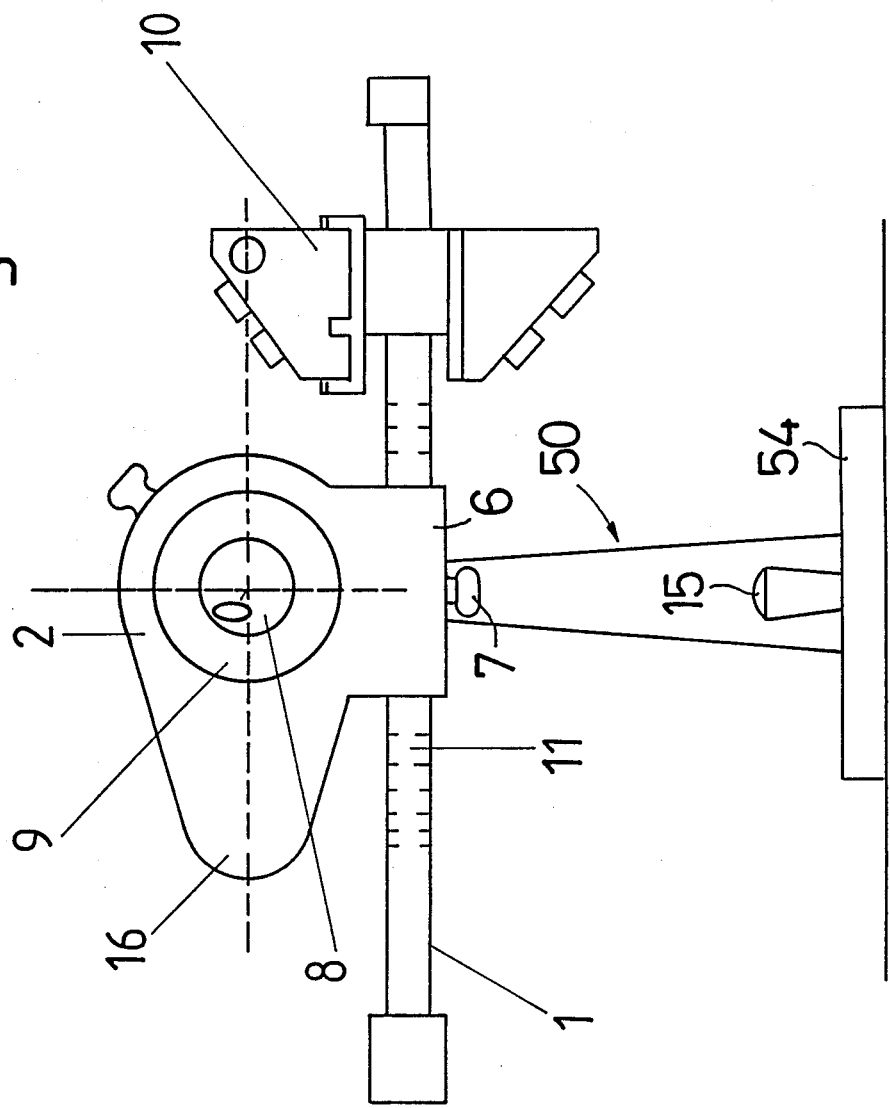
FIG. 2 is a front elevational view of the apparatus as seen from the left-hand side of FIG. 1, with the carrier member disposed in a substantially horizontal plane.
Figure 3:
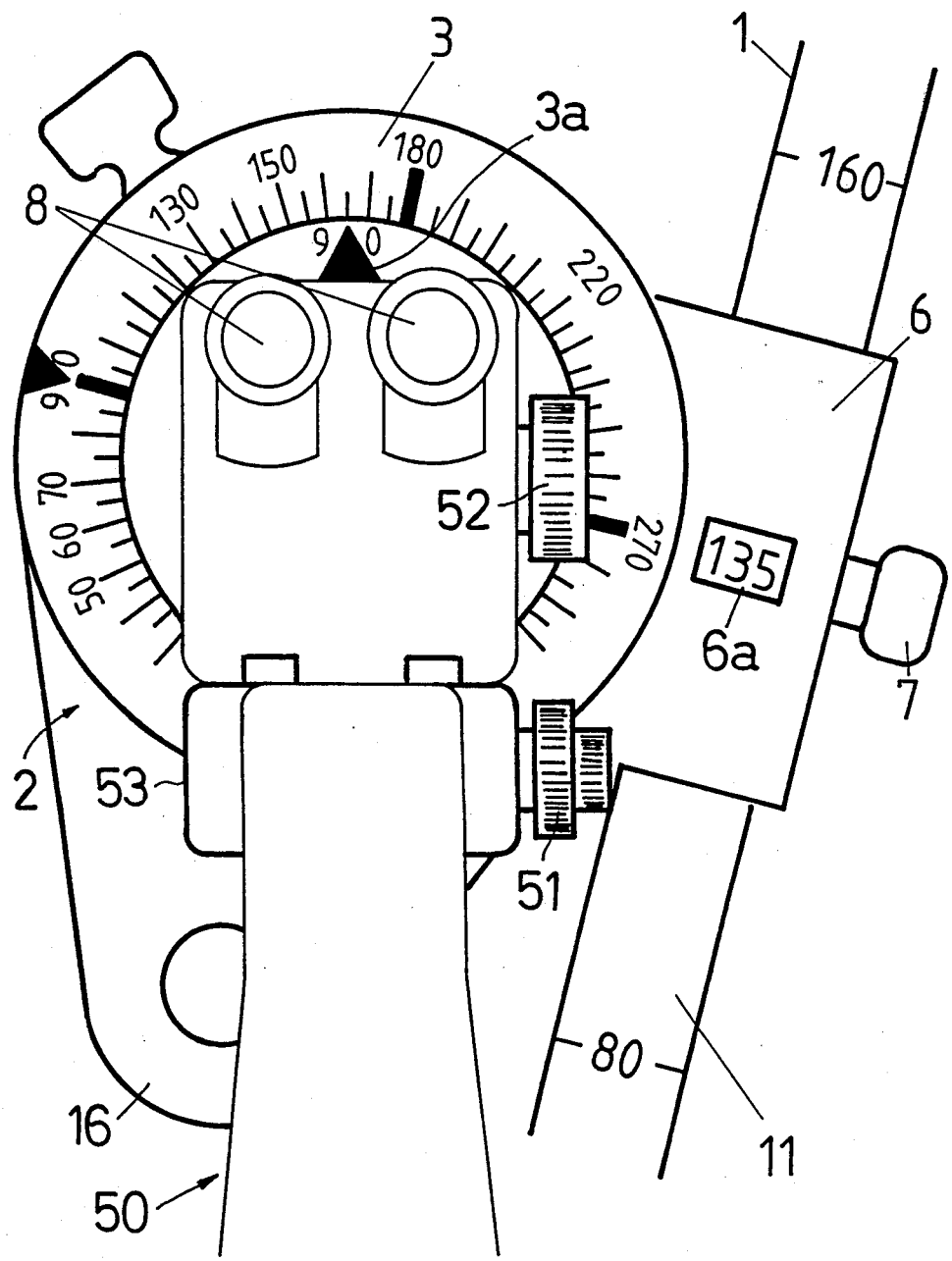
FIG. 3 is an enlarged fragmentary rear elevational view of the apparatus as seen from the right-hand side of FIG. 1, with the carrier member in a plane which makes an acute angle with the vertical plane of FIG. 1.

Referring first to FIG. 1, there is shown an apparatus wherein a floor-mounted holder 50 is connected with a support member 2 which mounts an imaging unit 8 and an arcuate carrier member 1. The latter is a curved body which extends along an arc of more than 180° and is movable relative to the support member 2 along an arcuate path between a practically infinite number of different positions including those shown in FIGS. 1 and 6. The support member 2 is movable with the imaging unit 8 and with the carrier member 1 in the direction of the optical axis 5 of the imaging unit toward or away from an object 0, e.g., a selected portion of the skin of a person occupying a chair or bed in such position that the selected portion of the skin is located in the focal plane of the objective of the imaging unit 8. The support member 2 is turnable about the optical axis 5 to thereby move the carrier member 1 to any one of a practically infinite number of different positions including those shown in FIGS. 1, 2 and 3. FIG. 3 shows that the support member 2 is provided with a graduated scale 3 whose graduations denote the inclination of an arm 6 for the carrier member 1 with reference to a selected plane, e.g., with reference to a vertical plane. As can be seen, the pointer 3a which cooperates with the scale 3 indicates that the plane of the carrier member 1 makes with such vertical plane an angle of 165°. A graduated scale 11 on the carrier member 1 is movable relative to the arm 6 of the support member 2, and the arm 6 has a window 6a which renders it possible to read the selected position of the carrier member 1 with reference to the support member; the window 6a indicates that the carrier member 1 has been moved through an angle of 135° with reference to an end position such as that shown in FIG. 6. The means for moving the carrier member 1 relative to the arm 6 of the support member 2 includes a knob 7 which is connected with a pinion (not specifically shown) in mesh with a toothed rack (not specifically shown) on the carrier 1. Alternatively, the knob 7 can simply carry a friction wheel which engages a portion of the carrier member 1 and moves the latter relative to the arm 6 in response to rotation of the knob 7. A wheel or knob 51 is provided to move the support member 2 along the holder 50 in the direction of the optical axis 5. A further wheel or knob 52 is provided to rotate the support member 2 with the imaging unit 8 about or relative to the optical axis 5. The directions of such movement of the support member 2 about the optical axis 5 are indicated in FIG. 1 by a double-headed arrow 4. If desired, the imaging unit 8 and the carrier member 1 can be mounted for movement relative to the support member 2 in or in parallelism with the direction of the optical axis 5. All that counts is to ensure that the imaging unit 8 as well as the object illuminating means of the improved apparatus can be moved to an optimum position for adequate illumination and imaging of the object 0, i.e., of a selected portion of the skin.

The illuminating means comprises an annular light source 9 which is preferably mounted on the support 2 and at least partially surrounds the objective of the imaging unit 8. In addition, the illuminating means comprises at least one light source 13 on the carrier 1. FIG. 1 shows that the carrier member 1 which is illustrated therein supports two light sources 13 each of which is mounted on a slide 10. The slides 10 are movable along the arcuate path which is defined by the carrier member 1 between any one of a finite or infinite number of different positions, and each light source 13 is further movable relative to the respective slide 10 in directions toward the object 0. The latter is located at or close to the center of curvature of the arc which is defined by the carrier member 1, and the light sources 13 are movable toward and away from such center of curvature along paths which are indicated in FIG. 1 by broken lines 12. The slides 10 and/or the light sources 13 are provided with means (indicated at 13a, 13b, 13c and 13d) for changing at least one characteristic of the light beam or beams which are emitted by the respective sources, for example, the size of the aperture or slot which is defined by a diaphragm to thus change the quantity of light impinging upon the object 0, the color of light, the intensity of light and/or one or more additional parameters which can influence the illumination of the object.

Movability of the imaging unit 8 in the direction of the optical axis 5 ensures that the objective of the unit 8 can be properly focused upon the selected portion of the skin, and movability of the light sources 13 with and relative to their slides 10 ensures that the selected portion of the skin can be illuminated in an optimum way during imaging of the selected portion of the skin, e.g., of an afflicted portion whose condition must be monitored at regular or irregular intervals. A scale 50a on the holder 50 indicates the selected position of the support member 2 with reference to the holder and hence the distance of the imaging unit 8 from the object 0 when the latter assumes a position at a known distance from the holder 50. The reference characters 14 denote in FIG. 1 mechanisms which are provided to move the light sources 13 with reference to the associated slides 10 along the respective paths 12. Suitable scales on the slides 10 furnish information as to the selected positions of the respective light sources 13.

In many instances, it suffices to illuminate the object only by light which issues from the source 9 or by light issuing from one or more sources 13 on the carrier member 1. The provision of illuminating means with light sources on the support member 2 as well as on the carrier member 1 ensures that any selected portion of the skin can be properly illuminated for the taking of pictures as well as that the selected porton of the skin can be illuminated by light having an optimum intensity, color and/or other desirable characteristics which can influence the quality of the recorded information.

The pedestal 54 of the holder 50 can be turned about a vertical axis in response to loosening of a locking device 15. This contributes to versatility of the apparatus. The reference character 16 denotes in FIG. 2 a counterweight which is provided on the support member 2 to compensate for unequal distribution of the combined weight of the carrier member 1, slides 10 and light sources 13.

The scale 11 on the carrier member 1 further serves to indicate the selected positions of the slides 10 relative to the carrier member.

At least some of the moving means (for the pedestal 54, for the support member 2 relative to the holder 50 in the direction of the optical axis 5, for the carrier member 1 relative to the support member 2, for the support member 2 about the optical axis 5, for the slides 10 along the carrier member 1 and/or for the light sources 13 relative to the respective slides 10) can be provided with suitable servomotors (not shown) and the movements can be initiated automatically in response to signals from a microprocessor or the like.

Figure 6:
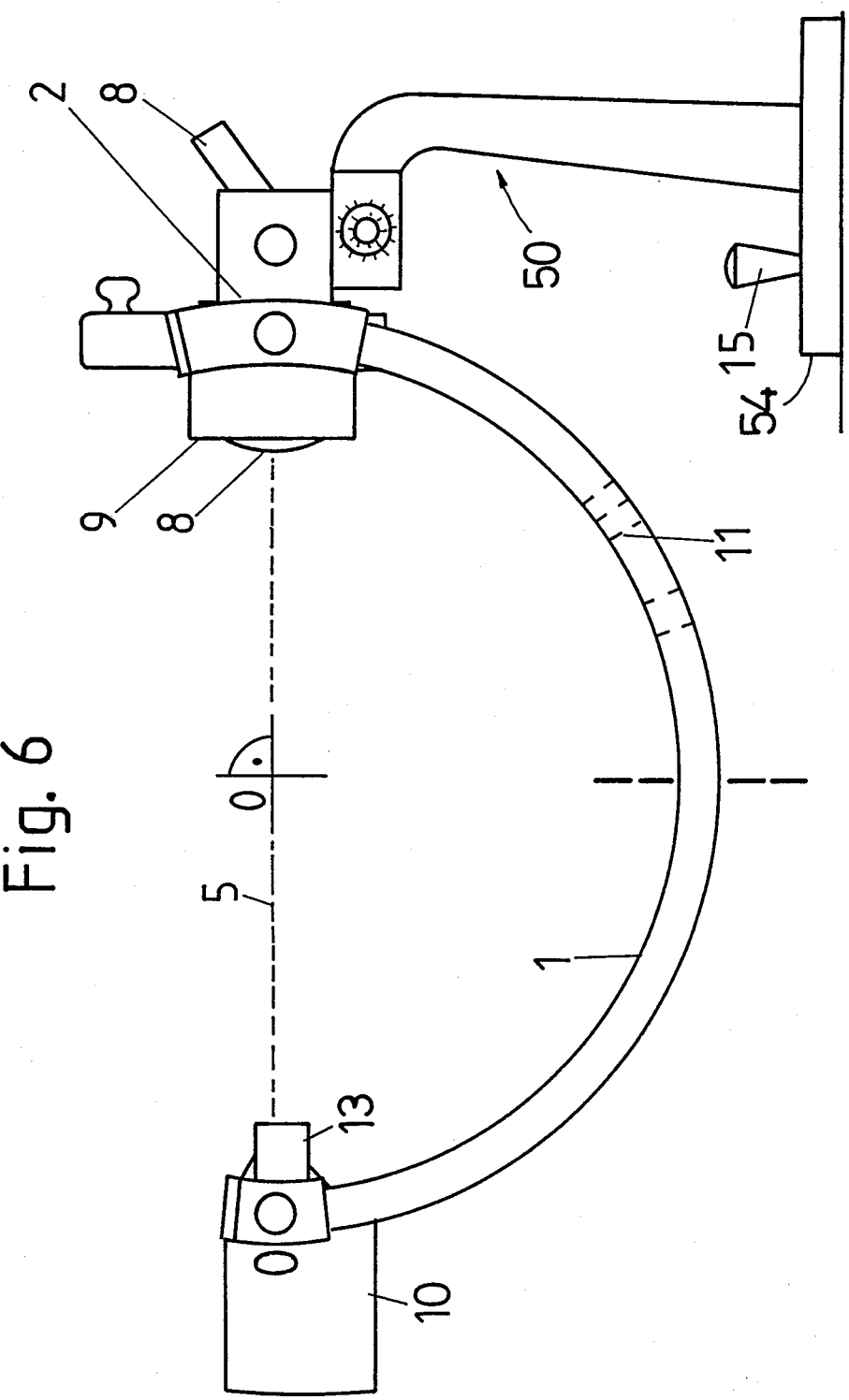
FIG. 6 is another side elevational view of the apparatus but showing the carrier member in a different position with reference to the support member for the imaging unit.

FIG. 6 shows that the apparatus can be set up to allow for transillumination of a selected skin portion (at 0). The selected skin portion (such as a swollen area) is located between a light source 13 on the carrier member 1 and the light source 9 on the support member 2. The carrier member 1 is shown in or close to one of its end positions with reference to the support member 2 and is located in a vertical plane. As explained above, the angular position of the carrier member 1 (with reference to the plane of FIG. 6) can be altered with or relative to the support member 2, for example, by turning the support member 2 about the optical axis 5. The intensity of radiation which is emitted by the light source 13 can be varied to ensure an optimum transillumination of the selected skin portion.

Figure 4:
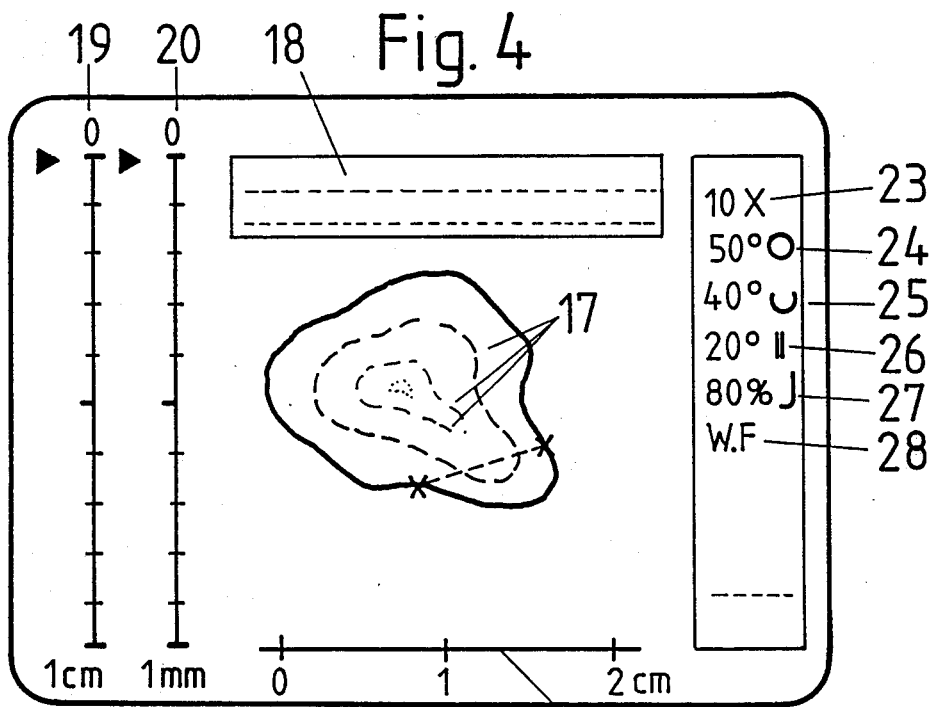
FIG. 4 illustrates the selected portion of the skin as seen through the objective of the imaging unit at a first distance from the selected portion of the skin.
Figure 5:
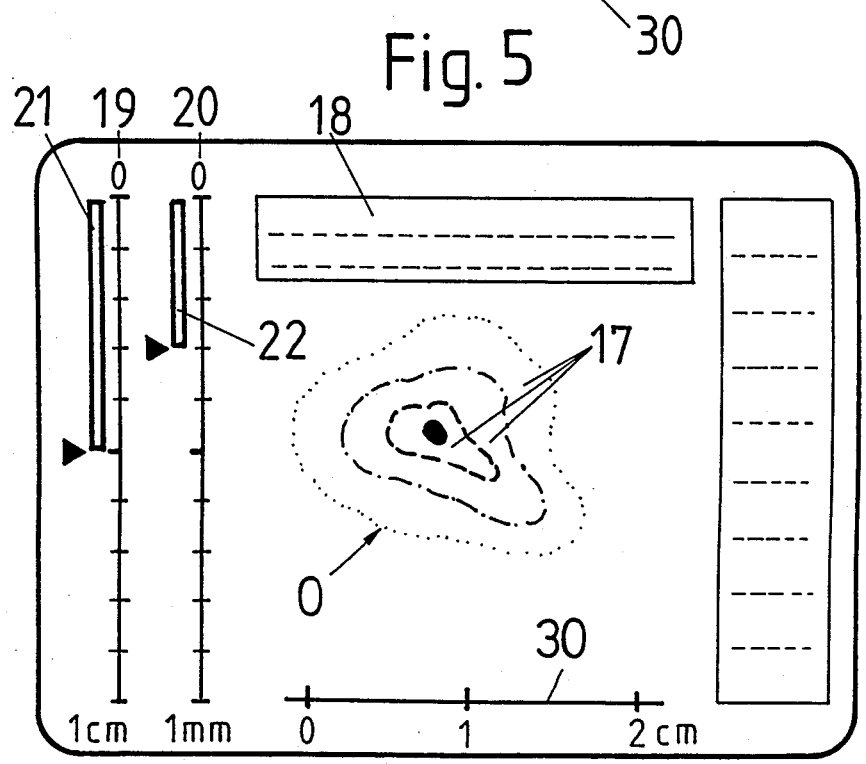
FIG. 5 illustrates the selected portion of the skin as seen through the objective when the imaging unit is located at a different second distance from the selected portion of the skin.
Figure 7:
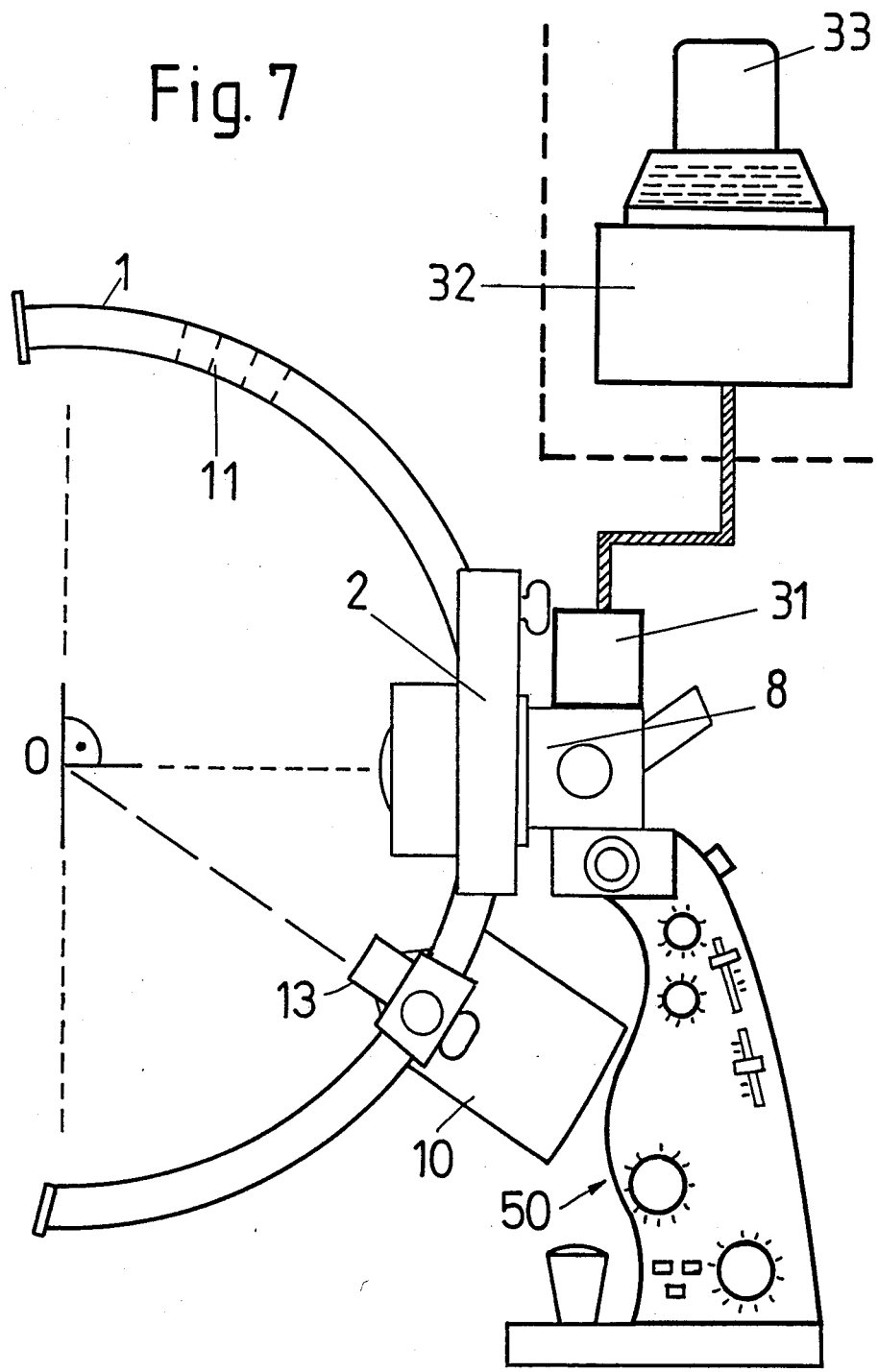
FIG. 7 is a side elevational view of a modified apparatus having a different holder for the support member and further including electronic evaluating and displaying means for the images of the selected portion of the skin.

FIGS. 4 and 5 illustrate the selected portion of the skin as it is seen in the field of view through the eyepieces of the imaging unit 8. The images which are shown in FIGS. 4 and 5 can be displayed by a monitor 33 which is shown in FIGS. 7 and 9. FIG. 4 shows the field of view in a first end position and FIG. 5 shows the field of view in a second end position of the imaging unit 8 with reference to the selected portion (0) of the skin on the optical axis 5. The focal plane 17 of the objective of the imaging unit 8 is shifted relative to the selected portion of the skin as a result of movement of the support member 2 and imaging unit 8, carrier member 1 and light source 9 in the direction of the optical axis 5. This renders it possible to produce sharp images of different regions of the selected skin portion. FIG. 4 shows a sharp image of the deepmost or rearmost region of the selected skin portion, and FIG. 5 shows a sharp image of the topmost or foremost region of such selected skin portion. In other words, the operator of the apparatus can take a series of pictures at different distances from the skin part surrounding the selected skin portion (object) 0. This renders it possible to record the color and the dimensions of each of a number of regions or zones of the selected skin portion 0 for comparison with the same regions or zones during the next-following or preceding examination.

The field 18 above the image of the selected skin portion 0 contains patient data (such as the age, sex, social security number and the like). The field at the left-hand side of the image of the selected skin portion is provided with scales 19 and 20 with pointers 21, 22 to indicate the dimensions of the selected skin portion 0. In the embodiment which is shown in FIGS. 4 and 5, the height of the skin portion 0 is 0.53 cm. The right-hand side of the image shown in FIGS. 4 and 5 is provided with a field for the displaying of information including at 23 the magnification factor, at 24 the angular position of the support member 2 with reference to the holder 50 (i.e., that graduation of the scale 3 which is pinpointed by 3a), at 25 the position of the carrier member 1 relative to the support member 2 (i.e., that graduation of the scale 11 which is seen in the window 6a of the arm 6), at 26 the setting of the diaphragm in the objective of the imaging unit 8, at 27 the intensity of light which is supplied by the source 9 and/or by the sources 13, and at 28 the color of light which impinges upon the selected portion of the skin.

A further scale 30 in the field of view of the objective of the imaging unit 8 renders it possible to ascertain the width of the selected skin portion 0. It will be seen that the apparatus can furnish information pertaining to all important factors which must be taken into consideration by a dermatologist in diagnosing an afflicted skin portion. The information which is seen in FIGS. 4 and 5 can be transmitted to a computer 32 (FIG. 7) which is connected to the imaging unit 8, together with a video camera 31 and the aforementioned monitor 33. The camera 31 transmits a microscopic image to the computer 32 for an analysis and for memorizing of the transmitted information. The monitor 33 can be used to directly display the information which is shown in FIGS. 4 and 5 as the examination of a selected skin portion progresses. Such information can include the image of the skin portion as well as all other data including the characteristics of light, the dimensions of the selected skin portion and the positions of various movable components relative to the holder 50 and relative to each other.

Figure 8:
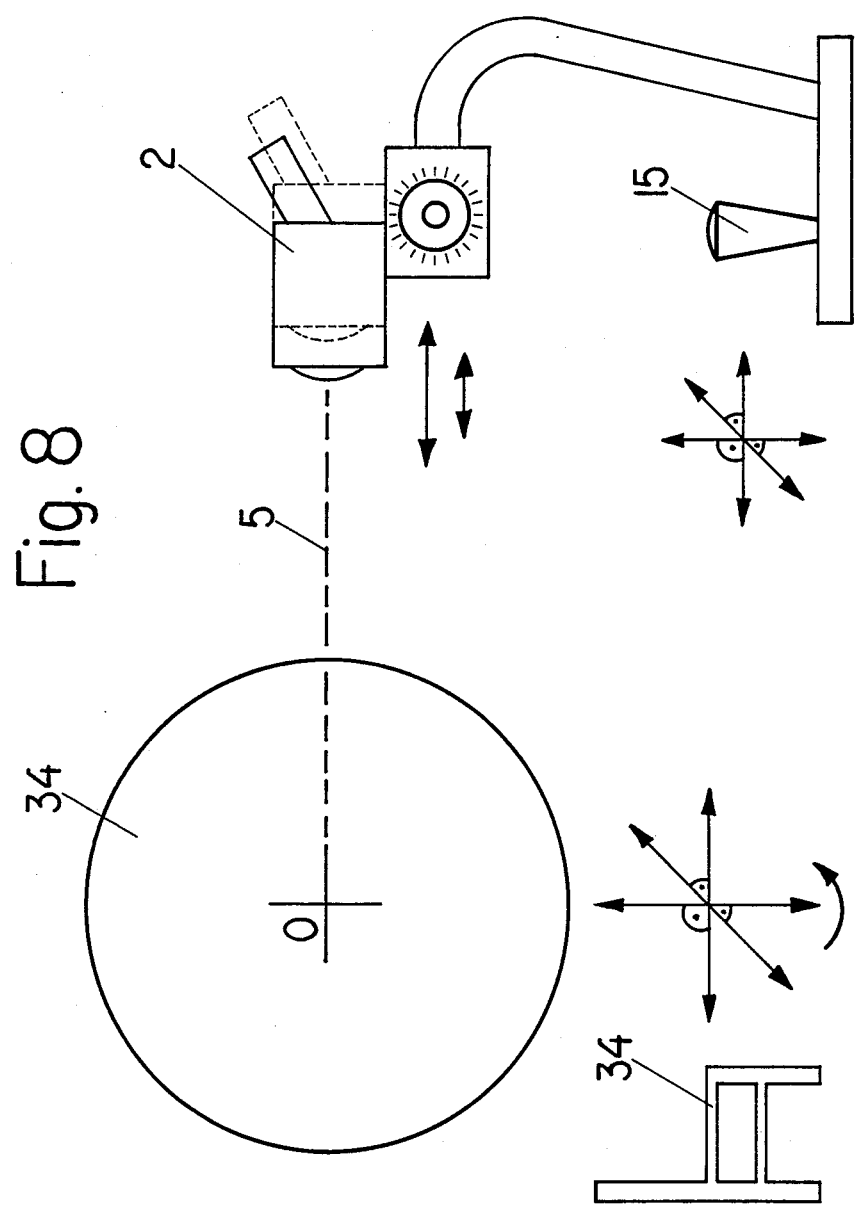
FIG. 8 is a schematic side elevational view of an apparatus which is similar to that of FIG. 1 and further showing a seating facility for the person to be examined with the apparatus.

FIGS. 8 and 9 show a chair 34 which is occupied by a patient during examination and which is preferably a universally movable chair so as to enable a dermatologist, a nurse or another person in charge to move the patient to an optimum position for examination of the afflicted skin portion. One of the persons in charge can look through the eyepieces of the imaging unit 8 while another person in charge observes the screen of the monitor 33. The carrier member 1 is omitted in FIGS. 8 and 9 for the sake of clarity. The imaging unit 8, the camera 31, the computer 32 and the monitor 33 are commercially available units. Suitable units are distributed by IBM, Zeiss, Leitz and many other makers of optical and electronic equipment.

An important advantage of the improved apparatus is its versatility. Thus, the apparatus can be set up to permit highly satisfactory illumination and examination of any, or practically any, selected skin portion and to permit the imaging of the selected skin portion in a number of different views including closeup shots as well as simultaneous recording of all other important information which is necessary for accurate and reliable determination of the healing process as well as of the nature of the affliction (e.g., whether benign or malignant). The illustrated illuminating means allows for satisfactory illumination (even transillumination) of the selected skin portion to ensure the making of satisfactory images.

Another important advantage of the improved apparatus is that it furnishes objective data regarding the condition of the selected skin portion. The stored information can be interpreted by any dermatologist regardless of language barriers.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should be and are intended to be comprehended within the meaning and range of equivalence of the appended claims.

I claim:

1. Apparatus for contact-free imaging and measurement of portions of skin, especially for diagnostic purposes, comprising at least one imaging unit having an optical axis and trainable upon a selected portion of skin; a support member means for supporting said imaging unit; an arcuate carrier member movably mounted on said support member means and extending along an arc of more than 90°, said arc having a center of curvature on or close to said axis, at least one of said members being movable in the direction of or relative to said optical axis; means for recording the position of said at least one member; and illuminating means including at least one first light source provided on said carrier member to illuminate the selected portion of the skin, said carrier member having means for moving said at least one first light source along said arc as well as toward and away from said center of curvature, and wherein said illuminating means further comprises a second light source at least partially surrounding said imaging unit.

2. The apparatus of claim 1, wherein said carrier member extends along an arc of more than 180°.

3. The apparatus of claim 1, further comprising a holder for said support member, said support member being turnable relative to said holder about said optical axis.

4. The apparatus of claim 1, wherein said support member is movable with said imaging unit in the direction of said optical axis.

5. The apparatus of claim 1, wherein said at least one first light source is movably installed on said carrier member and further comprising means for influencing the characteristics of light which is emitted by said at least one first source.

6. The apparatus of claim 5, wherein said characteristics include the intensity, color, direction and quantity of light.

7. The apparatus of claim 1, further comprising a video camera connected to receive the image captured by said imaging unit and wherein said camera has an output connected to a computer.

8. The apparatus of claim 1, further comprising a monitor connected with said imaging unit to display the image of the selected portion of the skin.

9. The apparatus of claim 1, further comprising means for rotating said support member about said optical axis.

10. The apparatus of claim 1, further comprising means for moving said at least one member.

* * * * *